(12) United States Patent
Gregg (10) Patent No.: US 9,091,619 B2
(45) Date of Patent: Jul. 28, 2015

(54) CIRCUMFERENTIAL SHEAR TEST METHOD AND APPARATUS FOR A SANDWICH STRUCTURE

(71) Applicant: The Boeing Company, Chicago, IL (US)

(72) Inventor: Paul S. Gregg, Seattle, WA (US)

(73) Assignee: The Boeing Company, Chicago, IL (US)

( * ) Notice: Subject to any disclaimer, the term of this patent is extended or adjusted under 35 U.S.C. 154(b) by 53 days.

(21) Appl. No.: 13/964,858

(22) Filed: Aug. 12, 2013

(65) Prior Publication Data

US 2015/0040680 A1     Feb. 12, 2015

(51) Int. Cl.
*G01N 3/24*     (2006.01)
*G01N 3/04*     (2006.01)
G01N 3/26     (2006.01)
G01N 3/56     (2006.01)
G01N 3/22     (2006.01)
G01N 3/08     (2006.01)

(52) U.S. Cl.
CPC .. *G01N 3/24* (2013.01); *G01N 3/04* (2013.01); *G01N 3/08* (2013.01); *G01N 3/22* (2013.01); *G01N 3/26* (2013.01); *G01N 3/562* (2013.01); *G01N 2203/0025* (2013.01)

(58) Field of Classification Search
CPC ............. G01N 3/08; G01N 3/22; G01N 3/24; G01N 3/26; G01N 3/562
USPC .................... 73/799, 845, 841, 829, 814, 815
See application file for complete search history.

(56) References Cited

U.S. PATENT DOCUMENTS

| | | | | |
|---|---|---|---|---|
| 3,839,905 | A | * 10/1974 | McCallen | ........................ 73/848 |
| 6,178,825 | B1 | * 1/2001 | Chang et al. | .................... 73/846 |
| 7,389,699 | B2 | * 6/2008 | Kelly et al. | ..................... 73/843 |
| 2007/0084296 | A1 | 4/2007 | Kelly et al. | |

FOREIGN PATENT DOCUMENTS

| | | |
|---|---|---|
| DE | 3828324 A1 | 2/1990 |
| SU | 800805 A1 | 1/1981 |
| SU | 922578 A2 | 4/1982 |

(Continued)

OTHER PUBLICATIONS

KO, "Comparison of Structural Behavior of Superplastically Formed / Diffusion-Bonded Sandwich Structure," Jun. 1980.

(Continued)

*Primary Examiner* — Lisa Caputo
*Assistant Examiner* — Tran M Tran (57) ABSTRACT

A test fixture for determining circumferential shear properties of an arcuate test specimen may include an outer fixture and an inner fixture. The outer fixture may be coupled to an outer side of the test specimen, and may be rotatably mounted on a central pin and may include a rocker arm. The inner fixture may be coupled to an inner side of the test specimen, and may be rotatably mounted on the central pin and may include a load arm extending in a direction opposite the rocker arm. The inner fixture and the outer fixture may be configured such that application of a test load to the rocker arm and the load arm causes rotation thereof about the central pin producing circumferential movement of the inner side relative to the outer side and inducing a circumferential shear load in the test specimen.

18 Claims, 10 Drawing Sheets

(56) References Cited

FOREIGN PATENT DOCUMENTS

SU          949393 A2      8/1982
WO     WO2012100780 A1     8/2012

OTHER PUBLICATIONS

Instron, "5900 Series Test Frames," retrieved from <http://www.instron.us/wa/product/5900-Series-Mechanical-Testing-Systems.aspx>, last visited Aug. 12, 2013.
ASTM, "Standard Test Method for Shear Properties of Sandwich Core Materials," ASTM C273, Mar. 2000.
Database WPI, Week 198324, Thomson Scientific, London, GB; AN 1983-J0765K, XP002733239 & SU 949 393 A2 (AZERB POLY), Aug. 7, 1982, WPI abstract, figure 1. (Cited in European Search Report dated Jan. 14, 2015).
Database WPI, Week 198144, Thomson Scientific, London, GB; AN 1981-L3939D, XP002733240 & SU 800 805 A1(BAKU MACH CONS WKS), Jan. 30, 1981, WPI abstract, figures 1-3. (Cited in European Search Report dated Jan. 14, 2015).
Database WPI, Week 198309 Thomson Scientific, London, GB; AN 1983-D0678K, XP002733241 & SU 922 578 A2 (AZERB POLY), Apr. 23, 1982, WPI abstract, figure 1. (Cited in European Search Report dated Jan. 14, 2015).

* cited by examiner

CIRCUMFERENTIAL SHEAR TEST METHOD AND APPARATUS FOR A SANDWICH STRUCTURE

FIELD

The present disclosure relates generally to structural testing and, more particularly, to testing systems for determining the shear properties of structures.

BACKGROUND

Sandwich structures are used in a wide variety of applications across a wise range of industries. Sandwich structures are constructed of a lightweight core bounded on opposing sides by face sheets. The face sheets may be formed of metallic material or non-metallic material. The core may have a cellular construction such as foam or honeycomb. The core may also be formed in a corrugated configuration or as a truss structure. Due to the relatively light weight of the core, sandwich structures advantageously have a relatively high stiffness-to-weight ratio as compared to solid metallic panels and solid composite laminates. In addition, sandwich structures have a relatively high strength-to-weight ratio due to the relatively low density of the core.

During the design and development of a sandwich structure, mechanical properties of the sandwich structure are used in material selection and sizing. For example, static and fatigue properties of the sandwich structure such as static shear modulus, shear strength, and shear fatigue may be used in selecting the material composition, geometry, and thickness of the core and the face sheets. Static and fatigue properties of curved sandwich structures have traditionally been characterized using data derived from the testing of flat sandwich test specimens. However, when a sandwich structure with a honeycomb core is formed into a curved shape, the static and fatigue properties of the sandwich structure can change significantly relative to the static and fatigue properties of a flat sandwich structure. In this regard, traditional design methods using flat panel test data may result in the use of inaccurate mechanical properties for a curved sandwich structure, and may result in design configurations that are un-conservative.

As can be seen, there exists a need in the art for a system and method for testing curved sandwich structures that accurately characterizes the structural properties of such curved sandwich structures. In this regard, there exists a need in the art for a system and method for testing curved sandwich structures that accounts for differences in the structural properties of a curved sandwich structure when the core, such as a honeycomb core, is formed in a curved shape.

SUMMARY

The above-noted needs associated with circumferential shear properties of curved sandwich structures are specifically addressed and alleviated by the present disclosure which provides a test fixture for determining circumferential shear properties of an arcuate test specimen. The test fixture may include an outer fixture and an inner fixture. The outer fixture may be coupled to an outer side of the test specimen, and may be rotatably mounted on a central pin and may include a rocker arm. The inner fixture may be coupled to an inner side of the test specimen, and may be rotatably mounted on the central pin and may include a load arm extending in a direction opposite the rocker arm. The inner fixture and the outer fixture may be configured such that application of a test load to the rocker arm and the load arm causes rotation thereof about the central pin producing circumferential movement of the inner side relative to the outer side and inducing a circumferential shear load in the test specimen.

In a further embodiment, disclosed is a test fixture for determining circumferential shear properties of a sandwich structure test specimen having an arcuate shape. The outer fixture may be coupled to an outer side of a test specimen. The test specimen may include a core and inner and outer face sheets. The test specimen may be formed in an arcuate shape defining a center of curvature. The outer fixture may be rotatably mounted on a central pin coaxial with the center of curvature. The outer fixture may include a rocker arm extending laterally outwardly relative to a loading axis of a test load applied to the test specimen. The test fixture may also include a pair of load arms (i.e., an inner fixture) positioned on opposite sides of the outer fixture. The load arms may be coupled to an inner side of the test specimen. The load arms may extend in a direction opposite the rocker arm and may be rotatably mounted on the central pin. The load arms and the outer fixture may be configured such that application of a test load to an end of each one of the rocker arm and the load arms causes rotation of the rocker arm and the load arm about the central pin producing circumferential movement of the inner face sheet and the outer face sheet relative to one another in response to rotating the rocker arm and the load arm, and inducing a circumferential shear load in the test specimen.

Also disclosed is a method of determining circumferential shear properties of an arcuate test specimen. The method may include coupling an outer side of a test specimen to an outer fixture having a rocker arm. The test specimen may have an arcuate shape defining a center of curvature. The outer fixture may be rotatably mounted on a central pin coaxial with the center of curvature. The method may further include coupling an inner side of the test specimen to an inner fixture rotatably mounted on the central pin and having a load arm extending in a direction opposite the rocker arm. The method may also include applying a test load to each end of the rocker arm and the load arm, and rotating the rocker arm and the load arm in opposite directions about the central pin in response to the test load. The method may additionally include producing circumferential movement of the inner side and the outer side relative to one another in response to rotating the rocker arm and the load arm, and inducing a circumferential shear load on the test specimen in response to producing circumferential movement.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
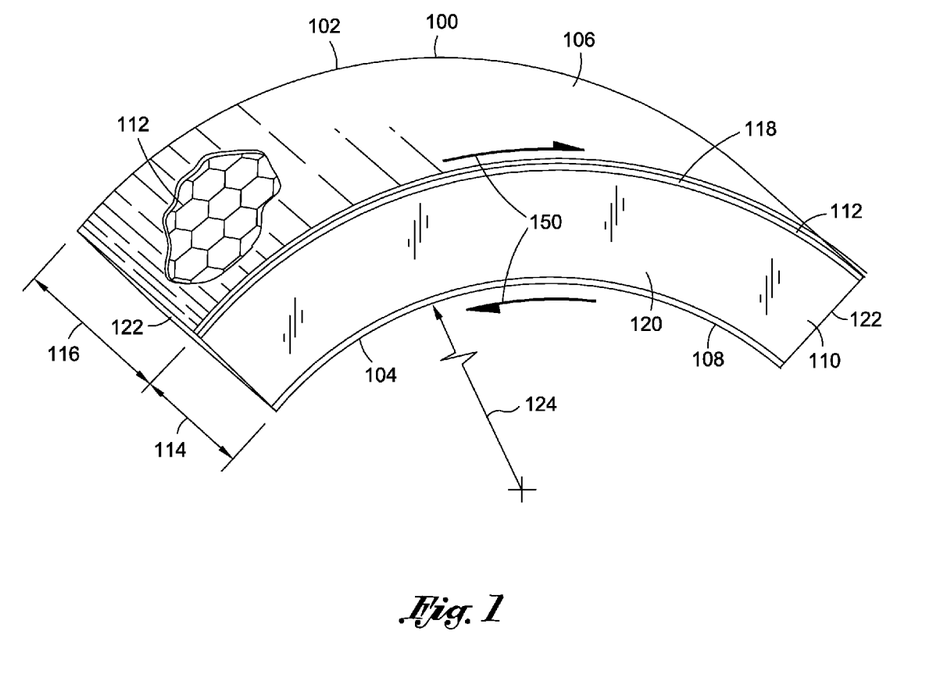
FIG. 1 is a perspective illustration of a test specimen having an arcuate shape and configured as a sandwich structure.

Referring now to the drawings wherein the showings are for purposes of illustrating various embodiments of the present disclosure, shown in FIG. 1 is a perspective view of a sandwich structure 102 test specimen 100 having an arcuate shape. The test specimen 100 may be mounted in a test fixture 198 (FIG. 2) as disclosed herein for determining the shear properties of the test specimen 100. For example, the test fixture 198 may provide a means for determining the circumferential shear properties of the test specimen 100 such as shear stiffness or modulus, static shear strength, and/or fatigue shear capability of the test specimen 100 in the circumferential direction.

In FIG. 1, the test specimen 100 is shown formed as a sandwich structure 102 having a core 112 interposed between an inner face sheet 108 and an outer face sheet 110. The test specimen 100 is shown formed in a ninety (90) degree arc segment having a radius of curvature of the inner face sheet 108 of approximately three (3) inches. The radius of curvature may define a center of curvature 124 for the test specimen 100. The test specimen 100 may be formed in any size arc segment and at any radius of curvature. The specimen may have a specimen thickness 114, and a specimen width 116 extending along an axial direction of the test specimen 100. The outer face sheet 110 and the inner face sheet 108 may each have an exposed outer surface. The test specimen 100 may have opposing specimen end faces 120 and opposing specimen side faces 122. As described below, an outer load plate 136 (FIG. 3) and an inner load plate 130 (FIG. 3) may be coupled to the respective outer side 106 and inner side 104 of the test specimen 100 to form a specimen assembly 128 (FIG. 3). The specimen assembly 128 may be mounted in the test fixture 198 (FIG. 2) as disclosed herein for generating circumferential shear load 150 on the test specimen 100.

In FIG. 1, the face sheets 108, 110 of the test specimen 100 may be formed of metallic or non-metallic material including titanium, aluminum, fiberglass, graphite epoxy, or any one of a variety of other materials or combination of materials. Although the core 112 is shown as a honeycomb core 112 in FIG. 1, the core 112 may be provided in any one of a variety of different configurations and may be formed of any one of a variety of different materials. For example, the core 112 may be provided as a foam core or as a truss structure (not shown). The core 112 may also be formed as a corrugated core. The core 112 may be formed from metallic material such as titanium, aluminum or other metallic materials, or the core 112 may be formed from non-metallic material such as fiberglass, aramid, paper, graphite-epoxy, and other non-metallic materials. The core 112 may be adhesively-bonded to the face sheets 108, 110 to form the test specimen 100. Alternatively, the sandwich structure 102 of the test specimen 100 may be constructed as a superplastically-formed/diffusion bonded structure (not shown) as known in the art.

Figure 2:
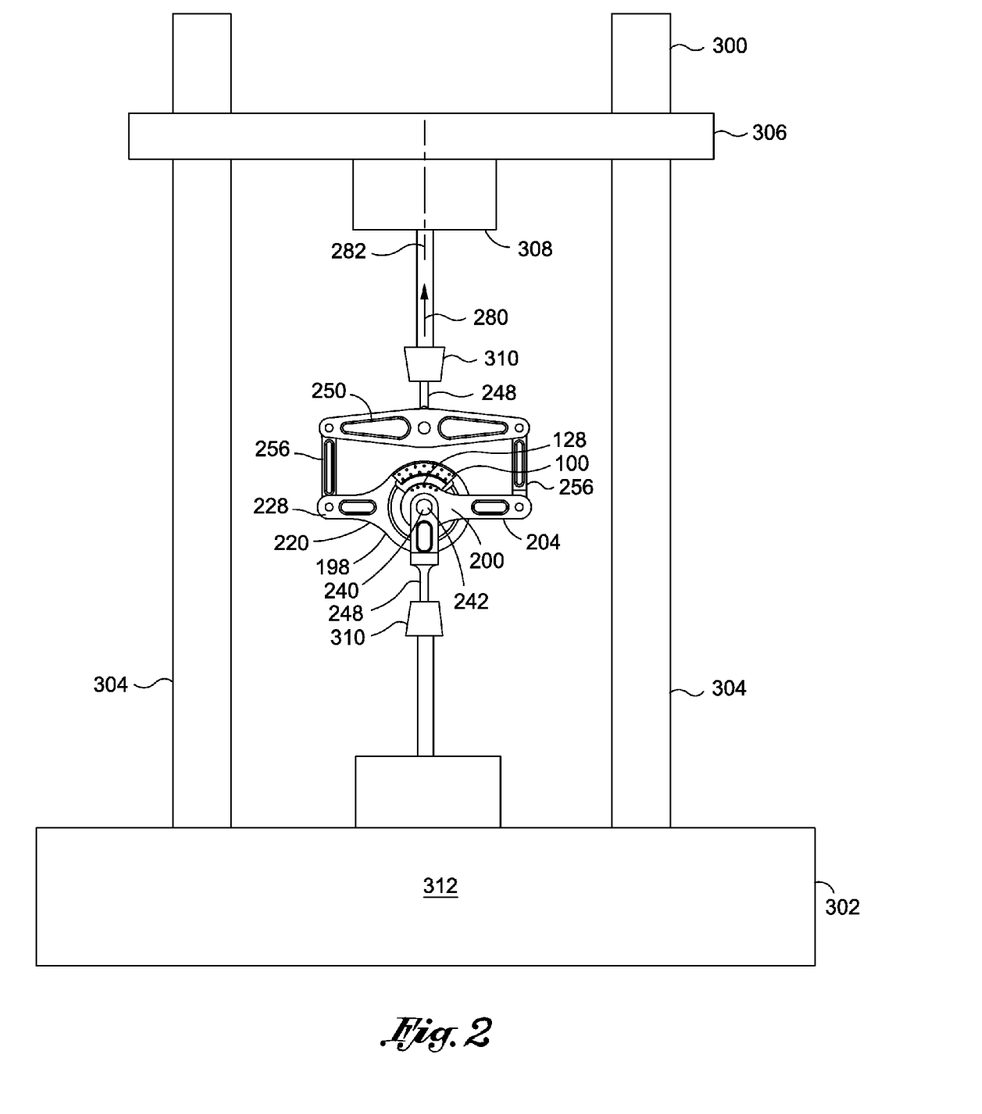
FIG. 2 is a side view illustration of an embodiment of a test frame having a test fixture installed in the test frame for inducing a circumferential shear load on an arcuate test specimen.
Figure 3:
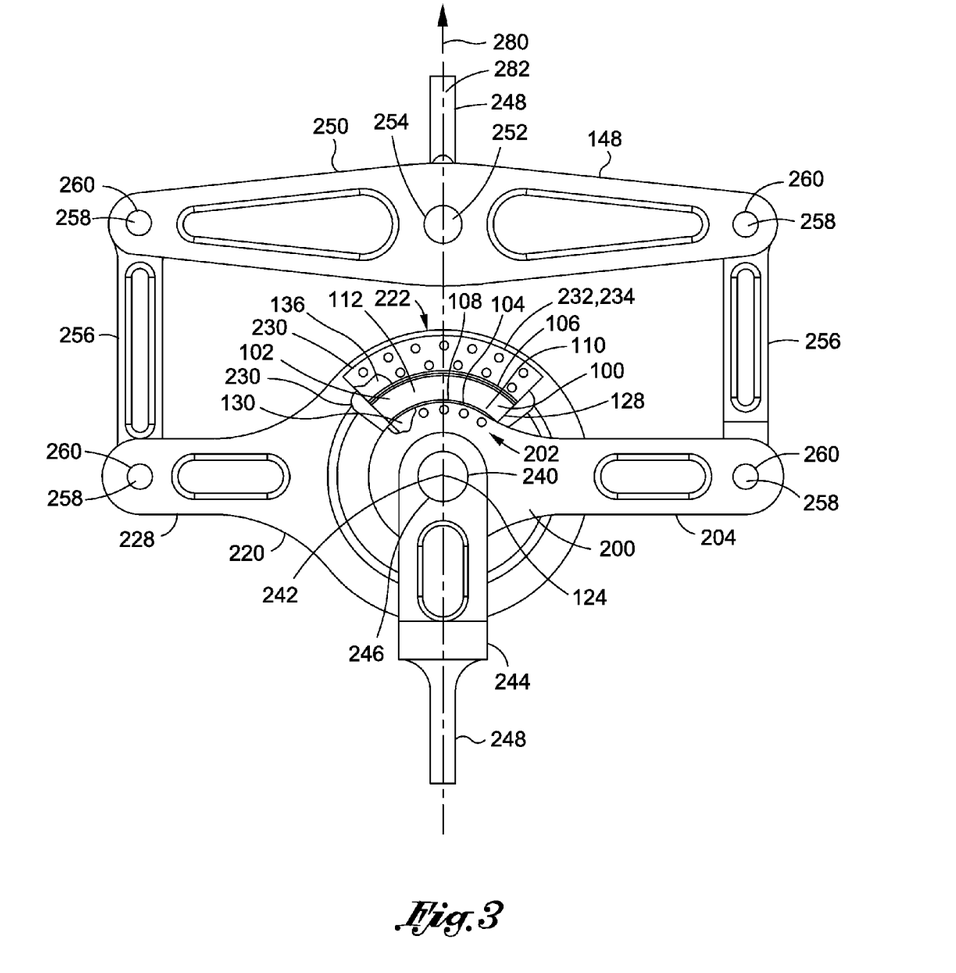
FIG. 3 is a side view of an embodiment of the test fixture.

In FIG. 2, shown is an embodiment of a test fixture 198 mounted in a test frame 300 for characterizing the shear capabilities of the test specimen 100. The test frame 300 may include a relatively rigid base 302 which may be mounted on a surface such as a floor of a test laboratory. The test frame 300 may include a plurality of posts or columns 304 that may extend upwardly from the base 302. The test frame 300 may include a crosshead 306 to interconnect the columns 304 at the top end of the test frame 300. The crosshead 306 may be vertically movable for applying a test load 280 to the test specimen 100 mounted in the test fixture 198. The test frame 300 may include one or more attachment fittings 310 for coupling the test fixture 198 to the test frame 300. In an embodiment, the attachment fittings 310 may be configured as pneumatic grips or hydraulic grips and may be quickly engaged for installing and removing the test fixture 198 from the test frame 300.

In FIG. 2, the test frame 300 may include an actuator 312 for moving the crosshead 306 up and down for applying the test load 280 to the test specimen 100 mounted within the test fixture 198. The test load 280 may be applied along a loading axis 282 of the test frame 300. The loading axis 282 may pass through the pivot axis 242 of the test fixture 198. The test frame 300 may include an actuator 312 for generating the test load 280. The actuator 312 may be hydraulically powered, electrically powered, mechanically powered, or the actuator 312 may be powered by other suitable means. The test frame 300 may include an axial load measuring device 308 such as a load cell. In the embodiment shown, the load measuring device 308 may they be coupled to an upper tension rod 248 extending upwardly from the test fixture 198. A lower tension rod 248 of the test fixture 198 may extend downwardly and may be coupled to a lower attachment fitting 310 of the test frame 300.

In FIG. 3, shown is a side view of an embodiment of the test fixture 198. The test fixture 198 may include an outer fixture 220 and an inner fixture 200. The outer fixture 220 may be coupled to the outer side 106 of the test specimen 100. The inner fixture 200 may be coupled to the inner side 104 of the test specimen 100. The outer fixture 220 may be generally disc-shaped and may include a rocker arm 228 extending laterally outwardly relative to a loading axis 282 of the test fixture 198. However, the outer fixture 220 may be provided in any one variety of sizes, shapes, and configurations for coupling to the outer side 106 of the test specimen, and is not limited to a disc shape.

Referring still to FIG. 3, the outer fixture 220 may be formed of relatively stiff or rigid material such as metallic material including steel, titanium, or other relatively stiff metallic or nonmetallic material for transmitting the test load

280 to the test specimen 100. The relatively high stiffness of the outer fixture 220 may result in substantially pure circumferential shear load 150 (FIG. 10) applied to the test specimen 100 with limited or negligible out-of-plane loading of the test specimen 100. In addition, the test fixture 198 may be configured such that the central pivot axis 242 is coaxial with the center of curvature 124 of the test specimen 100 such that substantially pure circumferential shear load is in induced in the test specimen 100.

In FIG. 3, the outer fixture 220 may include a cutout 236 in the area of the outer fixture coupling region 222. The cutout 236 may be sized and configured to receive the test specimen 100 or to receive the test specimen assembly 128. For example, the cutout 236 may have an arcuate shape to may match the arcuate shape of the test specimen 100 or specimen assembly 128. The specimen assembly 128 may include the test specimen 100 and an outer load plate 136 and inner load plate 130 adhesively bonded to or otherwise attached to the outer side 106 and the inner side 104 of the test specimen, as described below.

In FIG. 3, the outer fixture 220 may include an outer fixture central bore 226 for rotatably mounting the outer fixture 220 on a central pin 240 of the test fixture 198. The central pin 240 may define a central pivot axis 242 of the test fixture 198. The central pivot axis 242 may preferably be coaxial with the center of curvature 124 of the test specimen 100. The central pin 240 may be supported by a clevis fitting 244. The clevis fitting 244 may include a tension rod 248 extending downwardly and which may be coupled to an attachment fitting 310 (FIG. 2) of the test frame 300 (FIG. 2). The outer fixture 220 may include an outer fixture coupling region 222 for coupling the outer fixture 220 to the outer face sheet 110 of the test specimen 100. Alternatively, the outer fixture coupling region 222 may be coupled to the outer load plate 136 that may be bonded to the outer face sheet 110 of the test specimen 100.

In FIG. 3, the test fixture 198 may include one or more side plates 230 such as a pair of side plates 230 and which may be removably mounted on opposite sides of the outer fixture 220. The side plates 230 may include a plurality of coupling bores 232 that may extend through each side plate 230 and which may be aligned with a corresponding set of coupling bores 232 formed in the sides of the outer fixture 220 and in the end faces 138 of the outer load plate 136. One or more coupling pins 234 may be inserted into the coupling bores 232 to mechanically couple the outer fixture 220 to the outer load plate 136. However, the test fixture 198 may include other means for coupling the outer fixture 220 to the outer side 106 of the test specimen 100, and is not limited to side plates 230. For example, the test fixture 198 may include one or more mechanical features (not shown) that may be formed on the outer fixture 220 for engaging a complementary set of mechanical features (not shown) that may be formed on an outer surface of the outer load plate 136. Alternatively, the test fixture 198 may include mechanical features for engaging the outer fixture 220 to the opposing side faces 122 of the outer load plate 136.

As shown in FIG. 3, the inner fixture 200 may be coupled to the inner side 104 of the test specimen 100 and may be rotatably mounted on the central pin 240. For example, the inner fixture 200 may have an inner fixture coupling region 202 that may be coupled to the inner face sheet 108 of the test specimen 100, or to an inner load plate 130 of the specimen assembly 128. In the embodiment shown, the inner fixture 200 may comprise a pair of load arms 204 mounted on opposite sides of the outer fixture 220 and extending outwardly from the loading axis 282 in a direction opposite the rocker arm 228. Each one of the load arms 204 may have a central bore 208 that may be rotatably mounted on the central pin 240. The load arms 204 that make up the inner fixture 200 may be formed of relatively stiff or rigid material such as metallic material including steel, titanium, or other relatively stiff material for transmitting the test load 280 to the test specimen 100. As noted above with regard to the outer fixture 220, the relatively high stiffness of the load arms 204 may result in the application of substantially pure circumferential shear load 150 (FIG. 10) to the test specimen 100.

In FIG. 3, the load arm 204 on each side of the outer fixture 220 may have an inner face 206. The inner face 206 (FIG. 9) of each load arm 204 may be positioned in contacting relation to the end faces 132 (FIG. 6) of the inner load plate 130. Each one of the load arms 204 may include a plurality of coupling bores 232 extending axially through the load arm 204. A plurality of coupling bores 232 may also be formed in the end faces 132 of the inner load plate 130. A plurality of coupling pins 234 may be inserted into the coupling bores 232 to mechanically couple the load arms 204 to the inner load plate 130.

In FIG. 3, the test fixture 198 may include a spanner 250 which may be formed as a unitary structure. Alternatively, the spanner 250 may comprise a pair of spanners 250 mounted in side-by-side relation, and which may be coupled to the test frame 300 (FIG. 2) by means up a tension rod 248. The tension rod 248 may be coupled to the spanners 250 by means of a spanner pin 254 extending through a spanner bore 252 formed in the spanners 250 and the tension rod 248. The spanners 250 may couple the rocker arm 228 and the load arms 204 to the attachment fitting 310 (FIG. 2) of the test frame 300. A pair of side links 256 may interconnect the rocker arm 228 and the load arm 204 to the spanner 250 ends for transmitting the test load 280 to the rocker arm 228 and the load arm. The side links 256 may be coupled to the spanners 250 by means of link pins 260 extending into pin bores 258 formed in the side links 256 and in the spanner 250 ends. Similarly, the side links 256 may be coupled to the rocker arm 228 and load arm 204 by means of link pins 260 extending into pin bores formed in the ends of the rocker arm 228 and the load arm 204.

In an embodiment not shown, the test fixture 198 (FIG. 3) may be configured to allow for load-reversal of the test load 280 (FIG. 3) such as for fatigue testing of the test specimen 100 (FIG. 1). For example, instead of a clevis fitting 244 (FIG. 3) supporting the central pin 240, the central pin 240 (FIG. 3) may be fixedly secured to the test frame 300 (FIG. 2). The test fixture 198 may be configured to allow for the application of a reversible test load 280 (i.e., alternating upward and downward load) applied in equal magnitude to the ends of the rocker arm 228 (FIG. 3) of the outer fixture 220 (FIG. 3), and the ends of the load arm(s) 204 (FIG. 3) of the inner fixture 200 (FIG. 3). The reversible test load 280 may be applied for a predetermined quantity of loading cycles, as described below.

Figure 4:
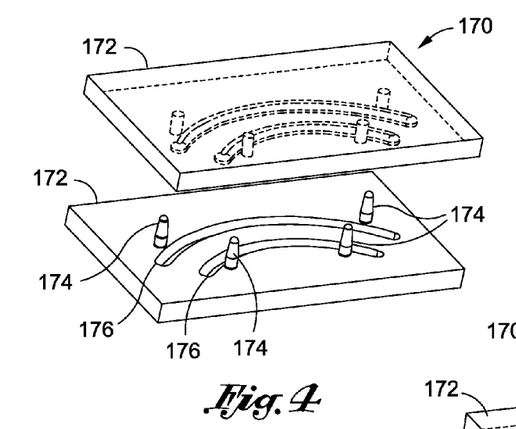
FIG. 4 is a perspective illustration of a pair of bonding plates of a bonding fixture for bonding inner and outer load plates to a test specimen to form a specimen assembly.

In FIG. 4, shown is a pair of bonding plates 172 of a bonding fixture 170 for bonding the inner load plate 130 (FIG. 6) and the outer load plate 136 (FIG. 3) to the test specimen 100 (FIG. 1) using an adhesive layer 142 (FIG. 5) between the load plate and the outer surfaces of the inner face sheet 108 (FIG. 3) and outer face sheet 110 (FIG. 3) of the test specimen 100. Each one of the bonding plates 172 may include one or more alignment pins 174 for engaging one or more of the coupling bores 232 (FIG. 3) formed in the end faces 132, 138 (FIG. 6) of the inner load plate 130 and the outer load plate. In addition, each one of the bonding plates 172 may optionally include an arcuate groove 176 at the location of the interface between the load plates 130, 136 and the face sheets 108, 110 of the test specimen 100.

Figure 5:
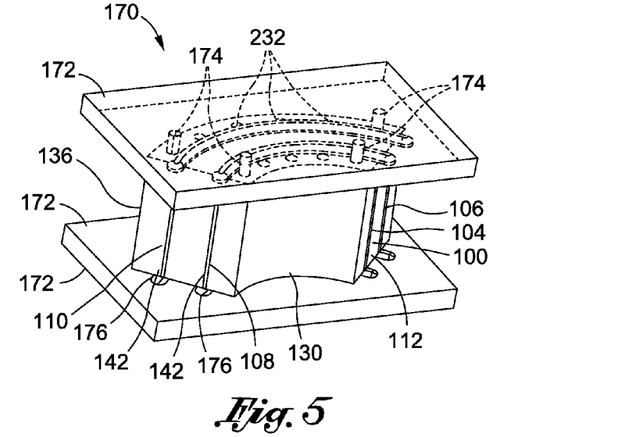
FIG. 5 is a perspective illustration of the inner plate, the outer plate, and the test specimen positioned between the bonding plates for holding such components in position during a bonding process to form the specimen assembly.

In FIG. 5, shown is the inner load plate 130, the outer load plate 136, and the test specimen 100 positioned between the bonding plates 172. The alignment pins 174 are engaged to the coupling bores 232 in the end faces 132, 138 (FIG. 6) of the load plates 130, 136. The engagement of the alignment pins 174 with the coupling bores 232 holds the outer load plate 136 in abutting contact with the outer surface of the outer face sheet 110, and the inner load plate 130 in abutting contact with the outer surface of the inner face sheet 108 during the process of curing the adhesive layer 142 bonding the load plates 130, 136 to the specimen assembly 128 (FIG. 3).

Figure 6:
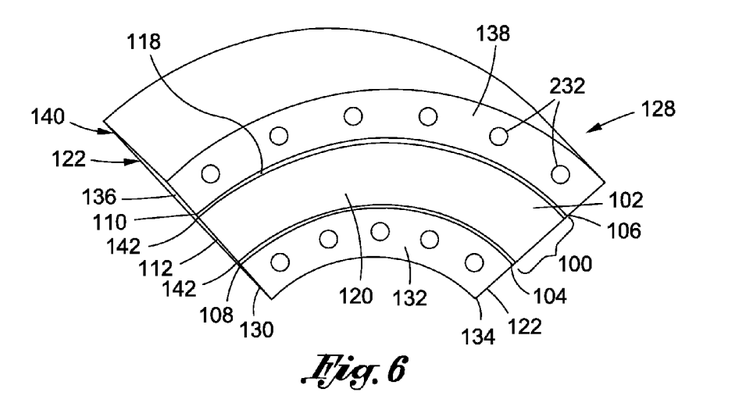
FIG. 6 is a perspective illustration of the specimen assembly.

In FIG. 6, shown is an embodiment of a completed specimen assembly 128. In the embodiment shown, the test specimen 100 is formed in an approximate ninety-degree arc segment and may be several inches in width in the axial direction. In addition, the test specimen 100 may be formed with a radius of curvature that substantially duplicates the radius of curvature of a structural article for which the shear properties are desired. The test specimen 100 may have a specimen thickness 114 (FIG. 1) comprised of a core 112 thickness and the face sheet thicknesses. The test specimen 100 may be formed in a size, shape, and geometry that substantially duplicates the geometry of an arcuate structural article for which circumferential shear properties are desired.

In FIG. 6, each one of the load plates may be formed in an arc length 118 (e.g., arc segment) and a width that may be similar to the arc length 118 and width 116 (FIG. 1) of the test specimen 100. In addition, the load plates 130, 136 may be sized and configured such that the inner load plate end faces 132 and the outer load plate end faces 138 are substantially flush with the specimen end faces 120. Likewise, the inner load plate side faces 134 and the outer load plate side faces 140 may be substantially flush with the specimen side faces 122. However, the load plates 130, 136 may be provided in different arc lengths and widths than the test specimen 100. It should be noted that the outer load plate 136 and inner load plate 130 may be coupled to the test specimen 100 by any means and are not limited to adhesive bonding. For example, the outer load plate 136 and the inner load plate 130 may be mechanically attached, brazed, or otherwise fastened to the respective outer side 106 (e.g., outer face sheet 110) and inner side 104 (e.g., inner face sheet 108) of the test specimen 100.

In FIG. 6, the test specimen 100 is sandwiched between the inner and outer load plate 130, 136 which advantageously improve the uniformity of loading of the test specimen 100 in shear. In this regard, the inner and outer load plate 130, 136 may be formed of relatively thick and/or stiff (e.g., relative to the core 112 stiffness of the test specimen) material such as steel or other metallic and non-metallic material. The relatively high stiffness of the inner and outer load plate 136 may limit movement of inner and outer face sheets 108, 110 of the test specimen 100 to substantially circumferential movement or displacement. In this regard, the relatively high stiffness of the inner and outer load plates 130, 136 may result in substantially pure shear strain in the test specimen 100 during the application of the test load 280 to the test specimen 100.

Figure 7:
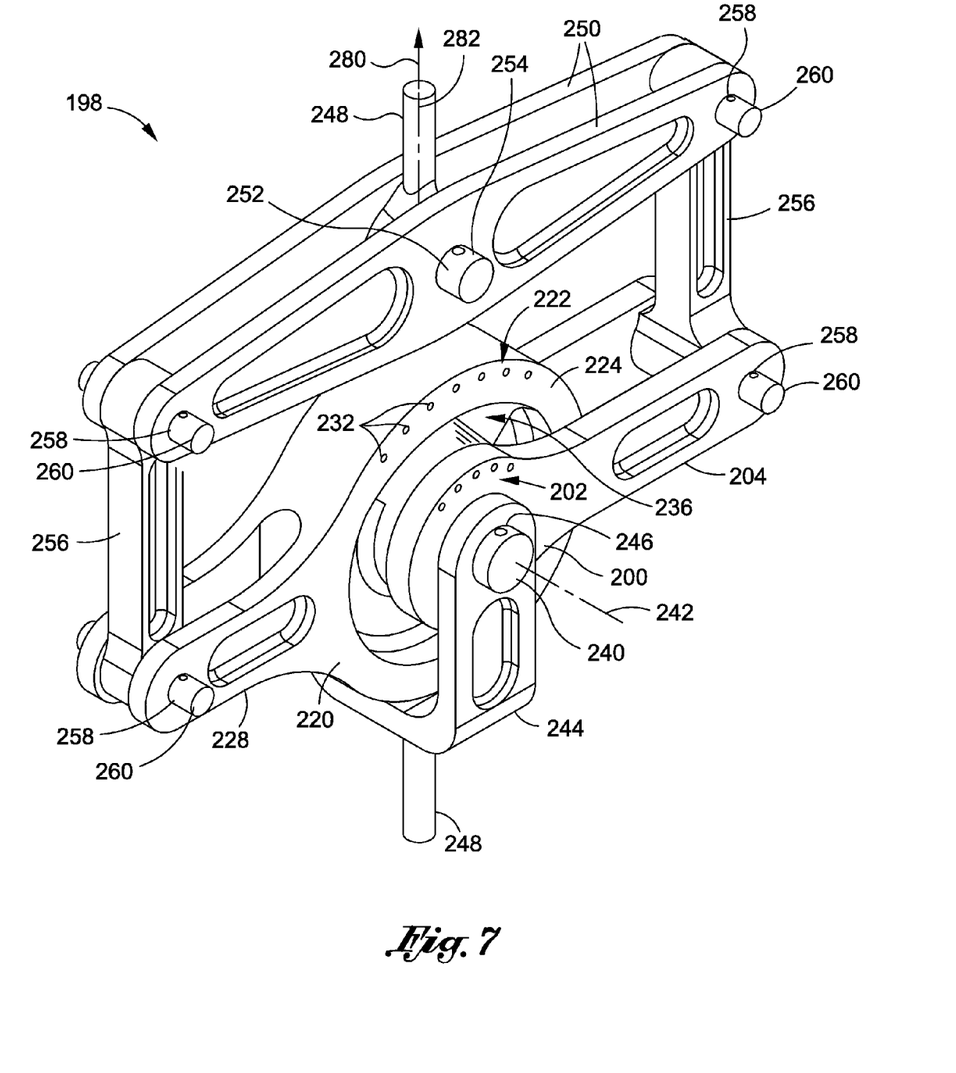
FIG. 7 is a perspective illustration of the test fixture with the specimen assembly omitted.

In FIG. 7, shown is a perspective illustration of the test fixture 198. The side plates 230 (FIG. 3) are removed to illustrate the cutout 236 and the outer fixture 220. Also shown are the coupling bores 232 that may be formed in the outer fixture coupling region 222. The cutout 236 may be sized and configured similar to the geometry of the specimen assembly 128 shown in FIG. 6. In this regard, the cutout 236 in the outer fixture 220 may be sized and configured complementary to the outer surface of the outer load plate 136 (FIG. 6) and the inner surface of the inner load plate 130 (FIG. 6). Also shown in FIG. 7 are the coupling bores 232 that may be formed in the outer fixture coupling region 222. Installation of the specimen assembly 128 in the test fixture 198 may include removal of the central pin 240 from the clevis fitting 244. One of the load arms 204 (FIG. 3) may be removed to allow for removal and installation of the specimen assembly 128 within the cutout 236. The load arm 204 may be repositioned and the central pin 240 may be installed in the central bore 246, 208, 226 of the clevis fitting 244, the load arms 204, and the outer fixture 220.

Figure 8:
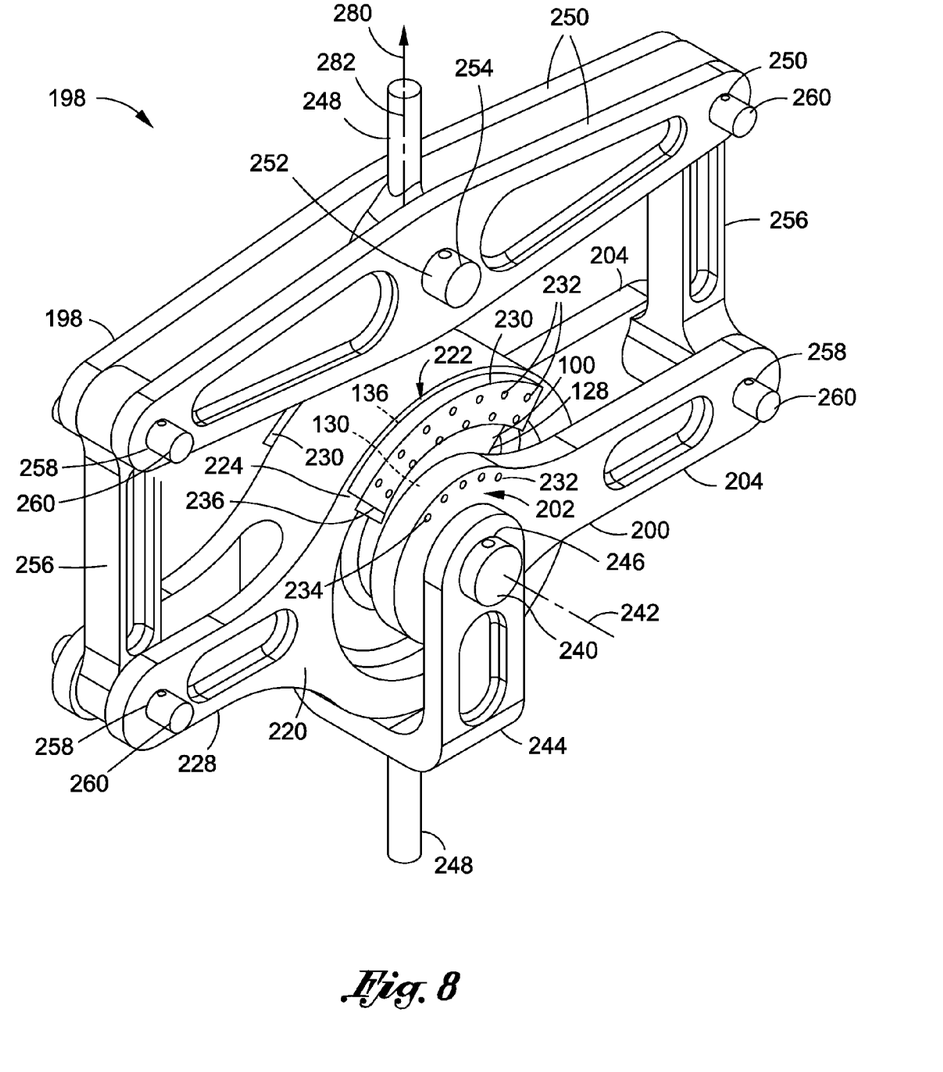
FIG. 8 is a perspective illustration of the test fixture with the specimen assembly coupled to an outer fixture and an inner fixture.

In FIG. 8, shown is the assembled test fixture 198 with the specimen assembly 128 coupled to the outer fixture 220 using a pair of side plates 230. As indicated above, a side plate 230 may be mounted on each side of the outer fixture 220. The coupling bores 232 in the side plates 230 may be aligned with coupling bores 232 in the outer fixture 220 and in the end faces 138 (FIG. 6) of the outer load plate 136. Coupling pins 234 may be inserted in the coupling bores 232 to fixedly secure the outer load plate 136 of the test specimen 100 to the outer fixture 220. In a similar manner, the coupling bores 232 and the load arms 204 on each side of the outer fixture 220 may be aligned with coupling bores 232 in the inner load plate 130. Coupling pins 234 may be inserted into the coupling bores 232 to fixedly secure the inner load plate 130 of the test specimen 100 to the load arms 204 of the inner fixture 200.

Figure 9:
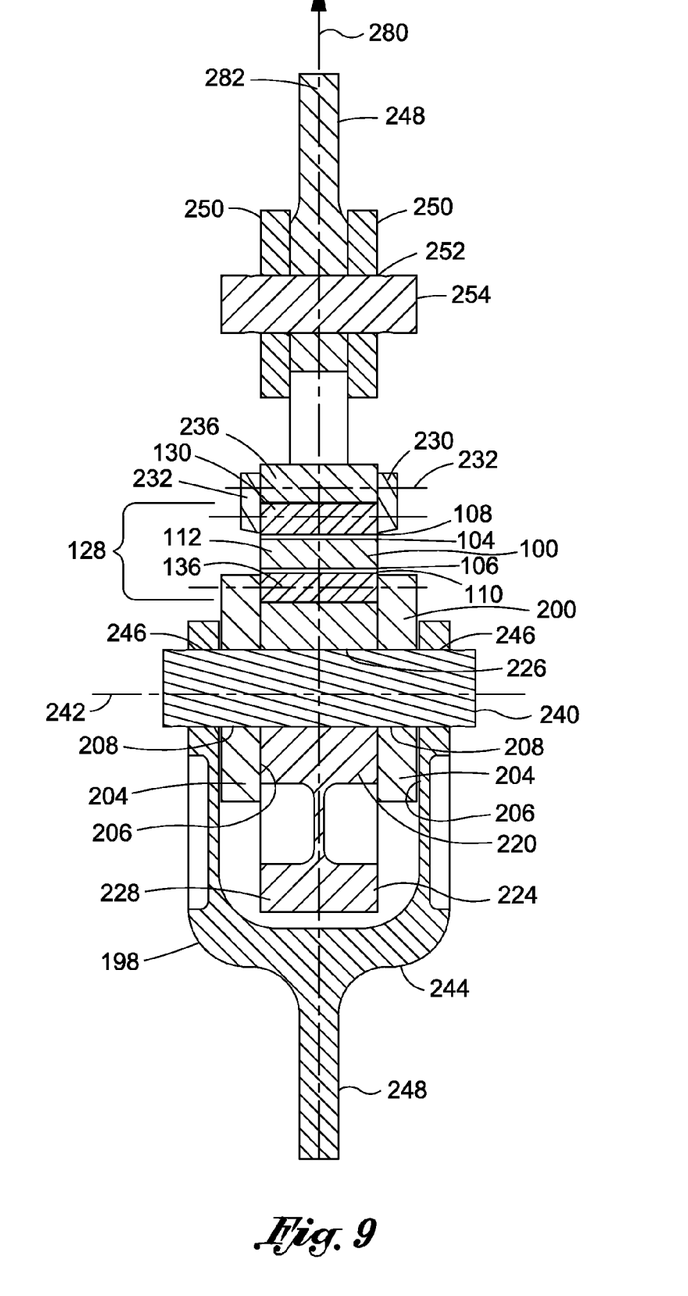
FIG. 9 is a sectional illustration of the test fixture showing the interconnection of the outer fixture and the inner fixture to the specimen assembly.

In FIG. 9, shown is a cross-sectional illustration of the test fixture 198 showing the specimen assembly 128 installed in the cutout 236 of the outer fixture 220. The side plates 230 on opposite sides of the outer fixture 220 overlap the outer load plate 136 of the specimen assembly 128. Likewise, the load arms 204 on opposite sides of the outer fixture 220 overlap the inner load plate 130 of the specimen assembly 128. Coupling pins 234 (FIG. 8), represented by centerlines in FIG. 9, may be inserted into coupling bores (not shown) for securing the side plates 230 to the outer load plate 136 and outer fixture 220, and for securing the load arms 204 (i.e., the inner fixture 200) to the inner load plate 130. The spacing between the flanges of the clevis fitting 244 may be sized complementary to the combined thickness of the load arms 204 and the outer fixture 220.

Advantageously, the test fixture 198 (FIG. 9) is configured to allow for relatively rapid disassembly to allow for rapid removal of a specimen assembly 128 (FIG. 9) following testing, and rapid installation of a new specimen assembly 128. The central pin 240 (FIG. 9) may be removed by removing one or more cotter pins (not shown) that may be inserted in the ends of the central pin 240. Likewise, the link pins 260 (FIG. 8) and the spanner pin 254 (FIG. 9) may also be removed by removing cotter pins or other mechanical features for locking the link pins 260 in position. The specimen assembly 128 may be disassembled by heating the specimen assembly to a softening temperature of the adhesive layer which bonds the inner and outer load plate 130, 136 (FIG. 9) to the respective inner and outer face sheet 108, 110 (FIG. 9). A new test specimen may be prepared by bonding, using the bonding fixture disclosed herein, the inner and outer load plate 130, 136 to the inner and outer face sheet 108, 110 of the new test specimen 100 (FIG. 9). The new specimen assembly 128 may be loaded into the test fixture 198 and testing may resume.

Figure 10:
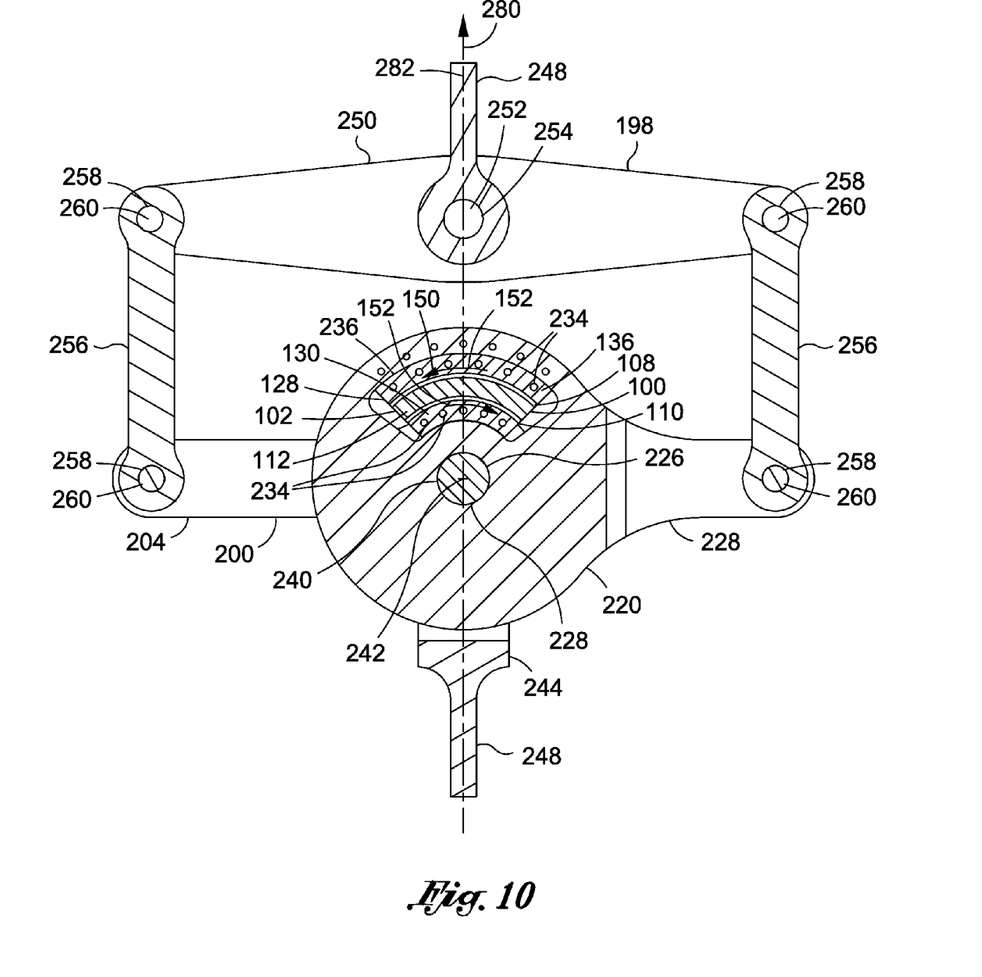
FIG. 10 is a sectional illustration of the test fixture showing the rocker arm and the load arm and the application of a test load for inducing a circumferential shear load on the test specimen.

In FIG. 10, shown is a cross-sectional view of the test fixture 198 and illustrating the application of a test load 280. As indicated above, the upper tension rod 248 of the test fixture 198 may be coupled to an upper attachment fitting 310 (FIG. 2) of the test frame 300. The lower tension rod 248 of the test fixture 198 may be coupled to a lower attachment fitting 310 (FIG. 2) of the test frame 300 (FIG. 2). Advantageously, the tension rods 248 may be configured to fit in standard grips (e.g., hydraulic grips or pneumatic grips) of a standard test frame 300 or universal testing machine. In this regard, the test fixture 198 may be sized and configured to allow for rotation of the test fixture 198 about the vertical loading axis 282 to provide easy access to the test fixture 198 for installing and removing specimen assemblies 128 from the test fixture 198 during a sequence of testing a plurality of test specimens 100.

In FIG. 10, the test load 280 is transmitted through the spanner 250 into the rocker arm 228 and the load arms 204. As indicated above, the rocker arm 228 extends laterally outwardly from one side of the loading axis 282. The load arms 204 extend laterally outwardly from an opposite side of the loading axis 282. The loading axis 282 may pass through the pivot axis 242 defined by the central pin 240. The pivot axis 242 may be oriented perpendicular to the loading axis 282. The load arm 204 has a load arm 204 length measured from the central pin 240 to the link pin 260 in the end of the load arm. Likewise, the rocker arm 228 has a rocker arm 228 length measured from the central pin 240 to the link pin 260 in the end of the rocker arm 228. The load arm 204 length is substantially equivalent to the rocker arm 228 length. The test load 280 applied to the upper tension rod 248 is reacted at the central pin 240.

In FIG. 10, the test load 280 is transmitted from the spanners 250 to the side links 256. The test load 280 pulls upwardly on the ends of the load arms 204 and rocker arm 228. As indicated above, the inner fixture 200 and the outer fixture 220 may be configured such that the application of the test load 280 to the ends of the rocker arm 228 and the load arms 204 causes rotation of the rocker arm 228 and outer load plate 136 along an outer plate rotational direction, and rotation of the load arms 204 and inner load plate 130 along an inner plate rotational direction opposite the outer plate rotational direction. For a sandwich structure 102 test specimen 100 having inner and outer face sheets 108, 110, rotation of the rocker arm 228 and the load arms 204 produces circumferential movement of the inner face sheet 108 and the outer face sheet 110 relative to one another, and inducing a circumferential shear load 150 in the test specimen 100.

Figure 11:
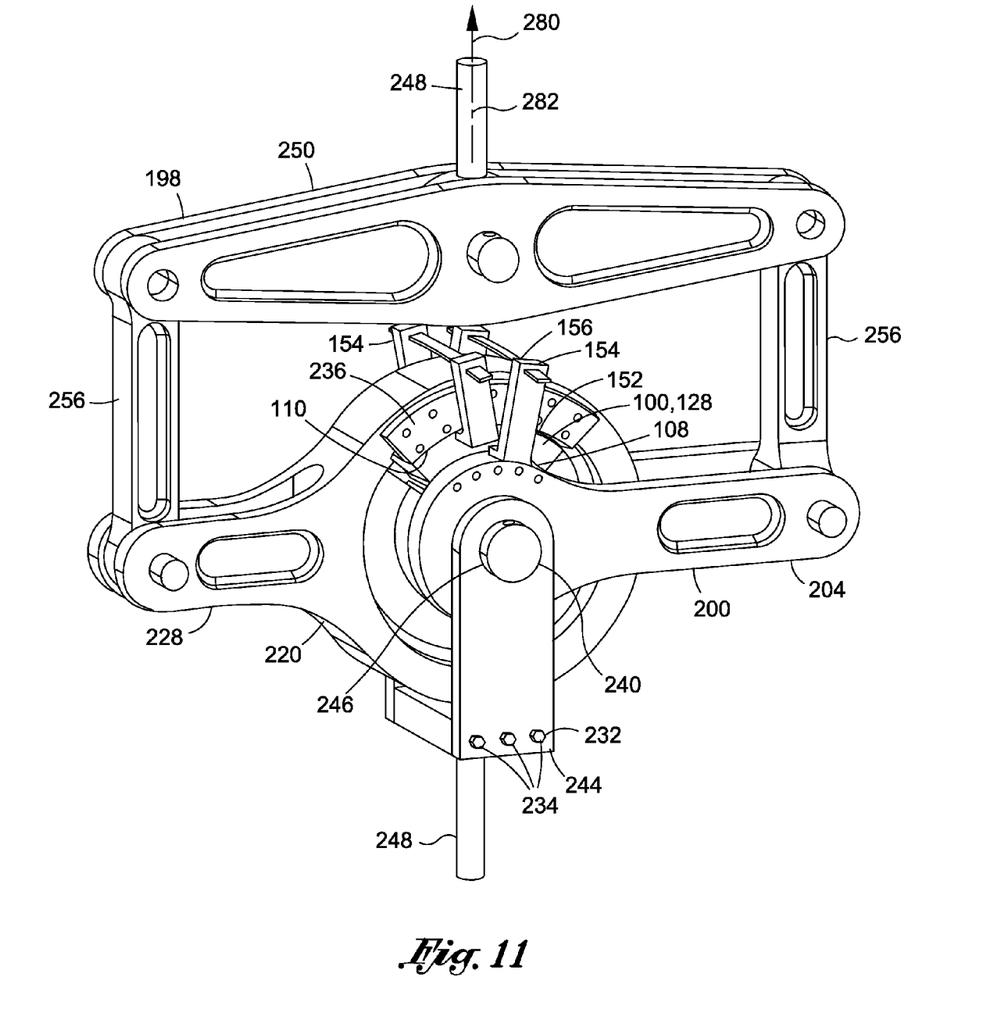
FIG. 11 is a perspective illustration of the test fixture with a displacement measurement device coupled to the test specimen for measuring circumferential displacement of an outer face sheet relative to an inner face sheet of the test specimen.

In FIG. 11, shown is a perspective illustration of the test fixture 198 with a displacement measurement device coupled to the specimen assembly 128. The displacement measurement device may be configured to measure circumferential displacement 152 of an outer face sheet 110 of the test specimen 100 relative to an inner face sheet 108 of the test specimen 100. In the embodiment shown, the displacement measurement device may comprise a pair of extensometers 156. One of the extensometers 156 may be coupled to the ends of the outer face sheet 110 on opposite ends of the test specimen, the other extensometer 156 may be coupled to the ends of the inner face sheet 108 on opposite ends of the test specimen 100. However, circumferential displacement 152 of the inner face sheet 108 relative to the outer face sheet 110 may be measured by any one of a variety of alternative displacement measuring devices (not shown) including, but not limited to, a deflectometer, a compressometer, a micrometer, a caliper, or by using an optical device such as a laser device, or other measurement devices.

Figure 12:
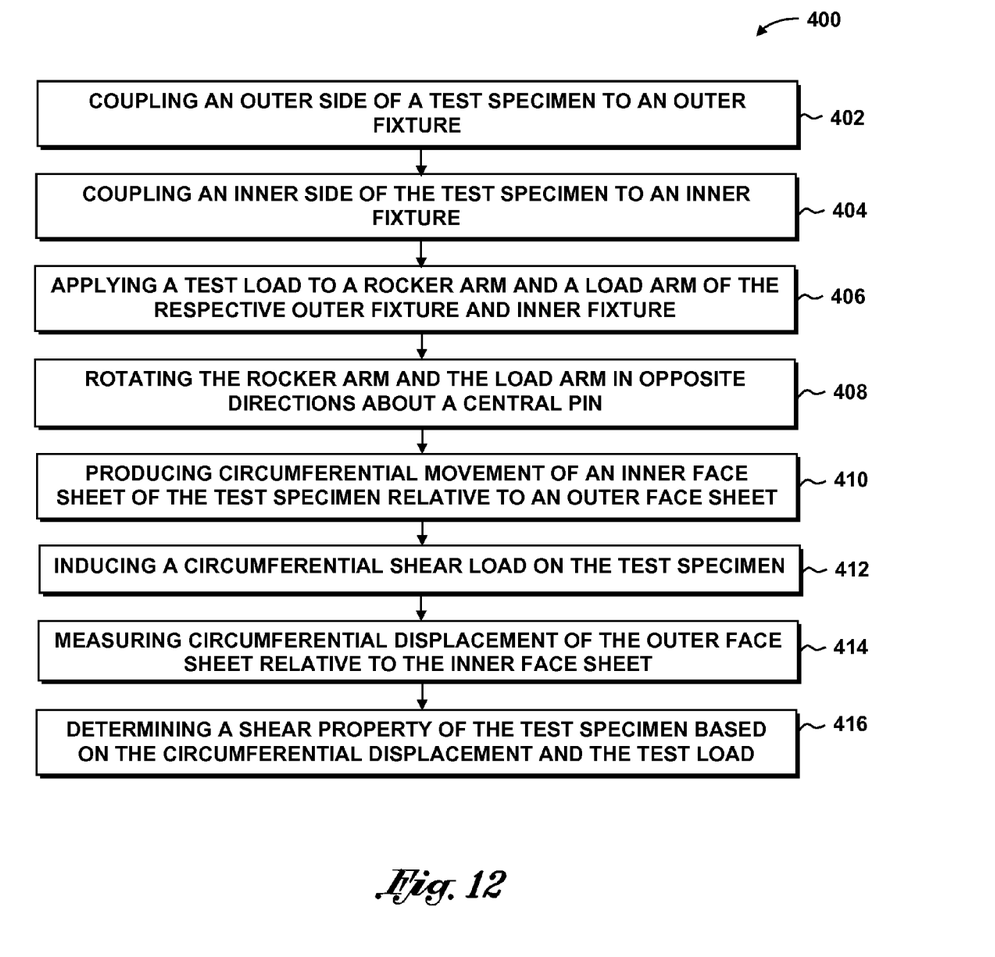
FIG. 12 is a flow chart including one or more operations that may be implemented in a method for determining the shear characteristics of an arcuate test specimen.

In FIG. 12, shown is a flow chart including one or more operations that may be implemented in a method 400 for determining the shear characteristics of an arcuate test specimen 100 (FIG. 1). The method will be described in the context of a sandwich structure 102 (FIG. 1) test specimen 100 having an inner face sheet 108 (FIG. 1), an outer face sheet 110 (FIG. 1), and a core 112 (FIG. 1), and with the test specimen 100 sandwiched between an inner load plate 130 (FIG. 3) and an outer load plate 136 (FIG. 3) as described above. However, the test method may be applied to any type of arcuate test specimen 100, and is not limited to a sandwich structure 102 test specimen 100.

Step 402 of the method 400 of FIG. 12 may include coupling the outer side 106 (FIG. 1) of the test specimen 100 to the outer fixture 220 (FIG. 2) which may include a rocker arm 228 (FIG. 2). As indicated above, the test specimen 100 (FIG. 1) is shown formed as a sandwich structure 102 (FIG. 1) having a core 112 (FIG. 1) interposed between an inner face sheet 108 (FIG. 1) and an outer face sheet 110 (FIG. 1). The test specimen 100 has an arcuate shape defining a center of curvature 124 (FIG. 1). The method may include loading the test specimen 100 in a cutout 236 (FIG. 3) formed in the outer fixture 220 (FIG. 3). The outer fixture 220 may be rotatably mounted on the central pin 240 (FIG. 3) which is coaxial with the center of curvature 124 (FIG. 3).

The test specimen 100 (FIG. 3) may be included in a specimen assembly 128 (FIG. 3) having an outer load plate 136 (FIG. 3) bonded to the outer side 106 (FIG. 3) or outer face sheet 110 (FIG. 3) of the test specimen 100, and an inner load plate 130 (FIG. 3) bonded to the inner side 104 (FIG. 3) or inner face sheet 108 (FIG. 3) of the test specimen 100. In this regard, the step of coupling the outer side 106 of the test specimen 100 to the outer fixture 220 (FIG. 3) may include coupling the outer fixture 220 to the outer load plate 136. For example, the method may include mechanically coupling, using a removable a pair of side plates 230 (FIG. 3), the outer faces 224 (FIG. 7) of the outer fixture 220 to the end faces 138 (FIG. 6) of the outer load plate 136.

Step 404 of the method 400 of FIG. 12 may include coupling the inner side 104 (FIG. 6) of the test specimen 100 (FIG. 6) to the inner fixture 200 (FIG. 3). As indicated above, the inner fixture 200 may include an opposing pair of load arms 204 (FIG. 3) positioned on opposite sides of the outer fixture 220 (FIG. 3). The load arms 204 may each be rotatably mounted on the central pin 240 (FIG. 3). The load arms 204 may extend in a direction opposite the direction of the rocker arm 228 (FIG. 3). For applications where test specimen 100 is provided in a specimen assembly 128 (FIG. 3) having inner and outer load plates 130, 136 (FIG. 6), the method may include coupling the inner fixture 200 or load arms 204 to the inner load plate 130. For example, each one of the load arms 204 may include a plurality of coupling bores 232 (FIG. 3). A plurality of coupling bores 232 may also be included in the end faces 132 (FIG. 6) of the inner load plate 130 (FIG. 6). The method may include inserting coupling pins 234 (FIG. 3) into the coupling bores 232 (FIG. 3) to mechanically couple the load arms 204 on each side of the outer fixture 220 to the end faces 132 (FIG. 6) of the inner load plate 130.

Step 406 of the method 400 of FIG. 12 may include applying a test load 280 to the end of the rocker arm 228 and to the end of the load arms 204. As shown in FIG. 10, the test load 280 may be reacted at the central pin 240. The test load 280 may be applied to the rocker arm 228 and the load arms 204 by using side links 256 to connect the rocker arm 228 and the load arms 204 to opposing spanner 250 ends of one or more spanners 250. The method may further include coupling the spanner 250 to the test frame 300 (FIG. 2) by coupling an upper tension rod 248 to an upper attachment fitting 310 (FIG. 2) of the test frame 300. The method may also include coupling the central pin 240 to a lower attachment fitting 310 of the test frame 300. In this regard, the test fixture 198 may include a clevis fitting 244 supporting the central pin 240. The clevis fitting 244 may include a lower tension rod 248 that may be coupled to the lower attachment fitting 310.

The upper and/or lower attachment fitting 310 (FIG. 2) may be configured as a hydraulic grip, a pneumatic grip, or other grip configurations. Application of the test load 280 (FIG. 10) to the spanner 250 (FIG. 10) may divide the test load 280 between the rocker arm 228 (FIG. 10) and the load arms 204 (FIG. 10). The method may include generating the test load 280 using the test frame 300 (FIG. 2) such as by moving the crosshead 306 (FIG. 2) of the test frame 300 in an upward direction. The method may additionally include transmitting the test load 280 through the spanner 250 and side links 256 (FIG. 10) and into the rocker arm 228 and load arms 204.

Step 408 of the method 400 of FIG. 12 may include rotating the rocker arm 228 and the load arms 204 in opposite directions about the central pin 240. In this regard, upon application of the test load 280 to the end of the rocker arm 228, the rocker arm 228 may be rotated along an outer plate rotational direction as shown in FIG. 10. The load arm 204 may be rotated along an inner plate rotational direction opposite the outer plate rotational direction.

Step 410 of the method 400 of FIG. 12 may include producing circumferential movement or displacement of the inner side 104 (FIG. 9) of the test specimen 100 relative to the outer side 106 (FIG. 9) of the test specimen 100 (FIG. 9). For test specimens 100 configured as a sandwich structure 102 (FIG. 6) having a core 112 and inner and outer face sheets 108, 110 (FIG. 9), the method may include producing circumferential movement of the inner face sheet 108 and the outer face sheet 110 relative to one another in response to rotating the rocker arm 228 (FIG. 9) and the load arms 204 (FIG. 9) in opposite directions. As indicated above, rotation of the load arms 204 may be transmitted to the inner load plate 130 (FIG. 9) of the specimen assembly 128 (FIG. 9) by the coupling pins 234 (FIG. 8) extending into the coupling bores 232 (FIG. 9) of the load arms 204. Rotation of the rocker arm 228 may be transmitted to the outer load plate 136 (FIG. 9) of the specimen assembly 128 (FIG. 9) by the coupling pins 234 extending into the coupling bores 232 of the side plate 230 (FIG. 9), outer fixture 220 (FIG. 9), and outer load plate 136.

Step 412 of the method 400 of FIG. 12 may include inducing a circumferential shear load 150 (FIG. 10) on the test specimen 100 (FIG. 10) in response to producing circumferential movement. Advantageously, the test fixture 198 (FIG. 10) is configured to produce substantially pure shear load in the test specimen 100 while minimizing out-of-plane loading of the test specimen 100. The substantially pure circumferential shear load 150 in the test specimen 100 may be due in part to the coupling of the test specimen 100 to the outer fixture 220 (FIG. 10) and the load arms 204 (FIG. 10) such that the center of curvature 124 (FIG. 3) is coaxial with the pivot axis 242 (FIG. 10) of the central pin 240 (FIG. 10). Furthermore, the central bores 208 (FIG. 9), 226 (FIG. 10) in the outer fixture 220 and the load arms 204 (i.e., the inner fixture 200) may be sized to provide a relatively low-tolerance fit onto the central pin 240 which may avoid radial movement of the outer fixture 220 and load arms 204 during application of the test load 280 (FIG. 10).

Step 414 of the method 400 of FIG. 12 may include measuring circumferential displacement 152 (FIG. 11) of the outer face sheet 110 (FIG. 11) of the test specimen 100 (FIG. 11) relative to the inner face sheet 108 (FIG. 11) when inducing the circumferential shear load 150 (FIG. 10) on the test specimen 100. In an embodiment, circumferential displacement 152 may be measured using one or more displacement measuring devices 154 (FIG. 11) such as extensometers 156 (FIG. 11). As indicated above, one extensometer 156 may be coupled to the inner face sheet 108 (FIG. 11) on opposite sides of the test specimen 100. Another one of the extensometers 156 may be coupled to the outer face sheet 110 on opposite sides of the test specimen 100. Alternatively, circumferential displacement 152 may be measured using alternative displacement measuring devices, and is not limited to extensometers 156.

Step 416 of the method 400 of FIG. 12 may include determining one or more shear properties of the test specimen 100 (FIG. 10) based on a magnitude of the test load 280 (FIG. 10) and the corresponding circumferential displacement 152 (FIG. 10). For example, the method may include recording test loads 280 increments on the test specimen 100 and the corresponding circumferential displacement 152 of the outer face sheet 110 (FIG. 10) relative to the inner face sheet 108 (FIG. 10) for each test load 280 increment. A load-displacement curve (not shown) may be generated based on the test load 280 increments and the corresponding circumferential displacement 152 of the outer face sheet 110 relative to the inner face sheet 108.

Circumferential shear stress may be calculated at a given location in the test specimen 100 (FIG. 10) based on the load-displacement data. For example, circumferential shear stress in the core 112 (FIG. 10) may be calculated for a given test load based on the magnitude of the circumferential shear load 150 (FIG. 10) at a given location in the core 112, such as at the core mid-plane (e.g., midway between the inner face sheet 108 and the outer face sheet 110), and based on the circumferential cross-sectional area of the core 112 at the given location (e.g., at the mid-plane). The circumferential static shear strength of the test specimen 100 may also be determined. For example, the shear yield strength and/or the ultimate shear strength of the core 112 in the circumferential direction may be determined based on the magnitude of the test load 280 (FIG. 10) at the yield point of the test specimen 100 and the ultimate load capability of the core 112. Circumferential shear strain may also be determined based on the circumferential displacement 152 (FIG. 10) of the outer face sheet 110 (FIG. 10) relative to the inner face sheet 108 (FIG. 10). Circumferential shear modulus of the core 112 may also be calculated based on a slope of the of above mentioned load-displacement curve and based on the relative circumferential displacement 152 (FIG. 10) the inner face sheet 108 and outer face sheet 110 and radial thickness of the core 112.

In an embodiment not shown, the method may include determining the fatigue shear characteristics of the test specimen 100 (FIG. 1). For example, the test fixture 198 (FIG. 7) may be configured to fixedly secure the central pin 240 (FIG. 7) in position on the test frame 300 (FIG. 2). The test fixture 198 may be configured such that the test load 280 (FIG. 7) may be reversibly applied to the load arm 204 (FIG. 7) and rocker arm 228 (FIG. 7) ends. For example, the method may include periodically reversing the direction of the test load 280 applied to the load arm 204 and rocker arm 228 ends. The test load 280 may be applied for a predetermined quantity of loading cycles. The circumferential fatigue shear strength of the test specimen 100 may be determined based on the magnitude of the test load 280 and the quantity of loading cycles.

Advantageously, static and fatigue structural properties for arcuate test specimens 100 (FIG. 7) may be accurately characterized using the test fixture 198 (FIG. 7) as disclosed herein. In this regard, the test fixture 198 advantageously improves the accuracy of the structural characterization of material properties of arcuate test specimens 100, and may lead to increased accuracy in the design and analysis of structures incorporating arcuately-shaped elements that are loaded in shear. Advantageously, the test fixture 198 may result in reduced maintenance and replacements costs of structural assemblies having arcuately-shaped structures.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A test fixture for determining circumferential shear properties of an arcuate test specimen, comprising: an outer fixture to which a test load is applied and configured to be coupled to an outer load plate having an arcuate shape and attached to an outer side of a test specimen having an arcuate shape, the outer fixture being rotatably mounted on a central pin and including an rocker arm; a side plate for mechanically couple the side of the outer fixture to the side of the outer load plate and transferring the test load from the outer fixture to the outer load plate; an inner fixture configured to be coupled to an inner side of the test specimen, the inner fixture being rotatably mounted on the central pin and including a load arm extending in a direction opposite the rocker arm; the inner fixture and the outer fixture being configured such that application of the test load to the rocker arm and the load arm causes rotation thereof about the central pin producing circumferential movement of the inner side relative to the outer side and inducing a circumferential shear load in the test specimen.

2. The test fixture of claim 1 wherein:
the outer fixture having a cutout configured to receive the test specimen.

3. The test fixture of claim 1 wherein:
the test specimen is formed as a sandwich structure having a core interposed between an inner face sheet and an outer face sheet; and
the outer load plate being attached to the outer face sheet.

4. The test fixture of claim 1 wherein:
the test specimen has an inner load plate attached to the inner face sheet; and
the inner load plate being mechanically coupled to the inner fixture.

5. The test fixture of claim 4 wherein:
the load arm has an inner face mechanically coupled to an end face of the inner load plate.

6. The test fixture of claim 1 further comprising:
a spanner having opposing spanner ends;
a pair of side links interconnecting the rocker arm and the load arm to the spanner ends; and
the spanner and the side links transmitting the test load to the rocker arm and the load arm.

7. The test fixture of claim 1 further comprising:
a clevis fitting configured to couple the central pin to a test frame.

8. The test fixture of claim 1 further comprising:
a displacement measuring device coupled to the test specimen and configured to measure circumferential movement of the inner side relative to the outer side.

9. A test fixture for characterizing circumferential shear properties of a sandwich structure test specimen having an arcuate shape, comprising: an outer fixture to which a test load is applied and configured to be coupled to an outer load plate having an arcuate shape and attached to an outer face sheet on an outer side of a test specimen including a core, an inner face sheet, and formed in an arcuate shape defining a center of curvature, the outer fixture being rotatably mounted on a central pin coaxial with the center of curvature, the outer fixture including a rocker arm extending outwardly; a side plate for mechanically coupling the side of the outer fixture to he side of the outer load plate and transferring the test load from the outer fixture to the outer load plate; a pair of load arms positioned on opposite sides of the outer fixture and being coupled to an inner side of the test specimen, the load arms extending in a direction opposite the rocker arm and being rotatably mounted on the central pin; and the load arms and the outer fixture being configured such that application of a test load to an end of each one of the rocker arm and the load arms causes rotation of the rocker arm and the load arm about the central pin producing circumferential movement of the inner face sheet and the outer face sheet relative to one another in response to rotating the rocker arm and the load arm, and inducing a circumferential shear load in the test specimen.

10. A method of determining circumferential shear properties of an arcuate test specimen, comprising the steps of:
mechanically coupling a side plate to an end face of an outer load plate and an end face of an outer fixture having a rocker arm; the outer load plate having an arcuate shape and being attached to an outer side of a test specimen, the test specimen having an arcuate shape defining a center of curvature, the outer fixture being rotatably mounted on a central pin coaxial with the center of curvature; mechanically coupling an inner side of the test specimen to an inner fixture rotatably mounted on the central pin and having a load arm extending in a direction opposite the rocker arm; applying a test load to each end of the rocker arm and the load arm; rotating the rocker arm and the load arm in opposite directions about the central pin; transferring, using the side plate, the test load from the outer fixture to the outer load plate; producing circumferential movement of the inner side and the outer side relative to one another in response to rotating the rocker arm and the load arm; and inducing a circumferential shear load on the test specimen in response to producing circumferential movement.

11. The method of claim 10 further comprising:
measuring circumferential displacement of an outer face sheet of the test specimen relative to an inner face sheet when inducing the circumferential shear load on the test specimen; and
determining at least one of the following shear properties of the test specimen based on a magnitude of the test load and corresponding circumferential displacement: circumferential shear stress for a given load, circumferential shear strain, circumferential shear modulus.

12. The method of claim 10 further comprising:
loading the test specimen in a cutout formed in the outer fixture.

13. The method of claim 10 wherein:
the test specimen is formed as a sandwich structure having a core interposed between an inner face sheet and an outer face sheet.

14. The method of claim 10 further comprising:
bonding the outer load plate to an outer face sheet of the test specimen;
bonding an inner load plate to an inner face sheet of the test specimen; and
mechanically coupling the inner fixture to the inner load plate.

15. The method of claim 14 further comprising:
mechanically coupling the load arm to an end face of the inner load plate.

16. The method of claim 14 further comprising:
connecting the rocker arm and the load arm to opposing spanner ends of a spanner using a pair of side links;
coupling the spanner to a test frame;
generating the test load using the test frame; and
transmitting the test load through the spanner and side links and into the rocker arm and load arm.

17. The method of claim 14 further comprising:
coupling, using a clevis fitting, the central pin to a test frame.

18. The method of claim 10 further comprising:
periodically reversing the direction of the test load applied to the rocker arm and load arm for a predetermined quantity of loading cycles; and
determining a fatigue shear strength based on a magnitude of the test load and the quantity of loading cycles.

* * * * *